United States Patent [19]

Sorensen

[11] Patent Number: 5,266,686
[45] Date of Patent: Nov. 30, 1993

[54] METHOD FOR ISOLATION AND PURIFICATION OF ENZYME-ANTIBODY CONJUGATES

[75] Inventor: Keld Sorensen, Roscoe, Ill.

[73] Assignee: Pierce Chemical Company, Rockford, Ill.

[21] Appl. No.: 951,224

[22] Filed: Sep. 25, 1992

[51] Int. Cl.$^5$ .................. C07K 3/20; C07K 17/10; A23J 3/24
[52] U.S. Cl. .................. 530/413; 530/350; 530/813; 435/188; 435/975; 435/177
[58] Field of Search .................. 530/350, 413, 813; 435/188, 7.9, 177, 7.92, 975

[56] References Cited

U.S. PATENT DOCUMENTS

| | | | |
|---|---|---|---|
| 4,504,585 | 3/1985 | Reynolds | 435/7.92 |
| 4,551,271 | 11/1985 | Hochuli | 530/351 X |
| 4,650,760 | 3/1987 | Chlebowski et al. | 435/7.6 |
| 4,877,830 | 10/1989 | Döbeli et al. | 525/54.3 |
| 5,047,324 | 9/1991 | Fredrickson | 435/188 X |
| 5,116,952 | 5/1992 | Martin et al. | 530/412 X |
| 5,169,936 | 12/1992 | Staples et al. | 530/350 |

FOREIGN PATENT DOCUMENTS 8501941 5/1985 World Int. Prop. O.

Primary Examiner—Michael G. Wityshyn
Assistant Examiner—C. Sayala

[57] ABSTRACT

A process is described for isolating an enzyme-antibody conjugate, wherein the enzyme is horseradish peroxidase or alkaline phosphatase, from an aqueous mixture of said conjugate and unconjugated enzyme. The process involves contacting the mixture with a water insoluble stationary phase having the $Ni^{+2}$ ion chelated thereto and binding said conjugate to the stationary phase. The phase containing bound conjugate is then washed to remove unbound enzyme. Thereafter the conjugate is eluted from the stationary phase and recovered in a form substantially free of the unconjugated enzyme.

8 Claims, 1 Drawing Sheet

METHOD FOR ISOLATION AND PURIFICATION OF ENZYME-ANTIBODY CONJUGATES

FIELD OF INVENTION

The present invention relates to the purification of enzyme-antibody conjugates and, more particularly to the isolation of conjugate from unconjugated enzyme.

BACKGROUND OF THE INVENTION

Enzyme-antibody conjugates are used in a number of immuno-assay techniques based on ligand-antiligand technology. The more common techniques are enzyme linked immunosorbent assays (ELISA), enzyme linked oligonucleotide immunosorbent assays (ELOSA) and immunoblotting. The antibodies most frequently used in the techniques are of the IgG and IgM type.

Customarily, the preparation of useful conjugates for immuno-assays involves the reaction of antibody with an excess of enzyme in order to achieve the most efficient and complete conjugation of antibody to enzyme. As a result of using excess enzyme, the conjugate reaction mixture will necessarily contain free, unconjugated enzyme. The free enzyme serves no beneficial purpose in immuno-assays and, in fact, causes nonspecific staining, called background staining.

Historically, methods which have been used to eliminate the presence of free enzyme after conjugate formation have not been totally satisfactory. Methods involving the use of extreme conditions, such as pH, can destroy or severely damage the enzyme part of the conjugate. More gentle procedures such as gel filtration are not generally applicable when large aggregates of enzyme are created, such as when glutaraldehyde is used to couple enzyme to antibody. When the enzyme of choice is alkaline phosphatase, a large and popular enzyme, purification by gel filtration presents particularly special problems.

SUMMARY OF THE INVENTION

In accordance with the present invention, there is provided a method, and associated kit, which can be used for isolating an enzyme-antibody conjugate, wherein the enzyme is horseradish peroxidase (HRP) or alkaline phosphatase (Alk. Phos.), from a mixture of the conjugate and free enzyme. The method described herein presents advantages over those methods commonly used for conjugate purification. The conditions used are mild and the method can be used on large conjugates. Use of the "purified" conjugate yields low background for blotting or ELISA or ELOSA procedures and improved signal to noise ratios.

In one of its aspects, the method described herein involves metal chelation chromatography utilizing the interaction of the $Ni^{+2}$ ion and the antibody to the exclusion of such interaction with the enzymes, HRP or Alk. Phos. Accordingly, an aqueous mixture of enzyme-antibody conjugate and free enzyme, wherein the enzyme is HRP or Alk. Phos., is contacted with a water insoluble stationary phase which has the $Ni^{+2}$ ion chelated to the phase. The conjugate chelates with the $Ni^{+2}$ ion whereas neither of the specified enzymes do so. Subsequent washing of the phase with a mild buffer removes unbound enzyme. The conjugate can then be eluted from the phase and recovered in a form substantially free of unconjugated enzyme.

DESCRIPTION OF INVENTION

Figure 1:
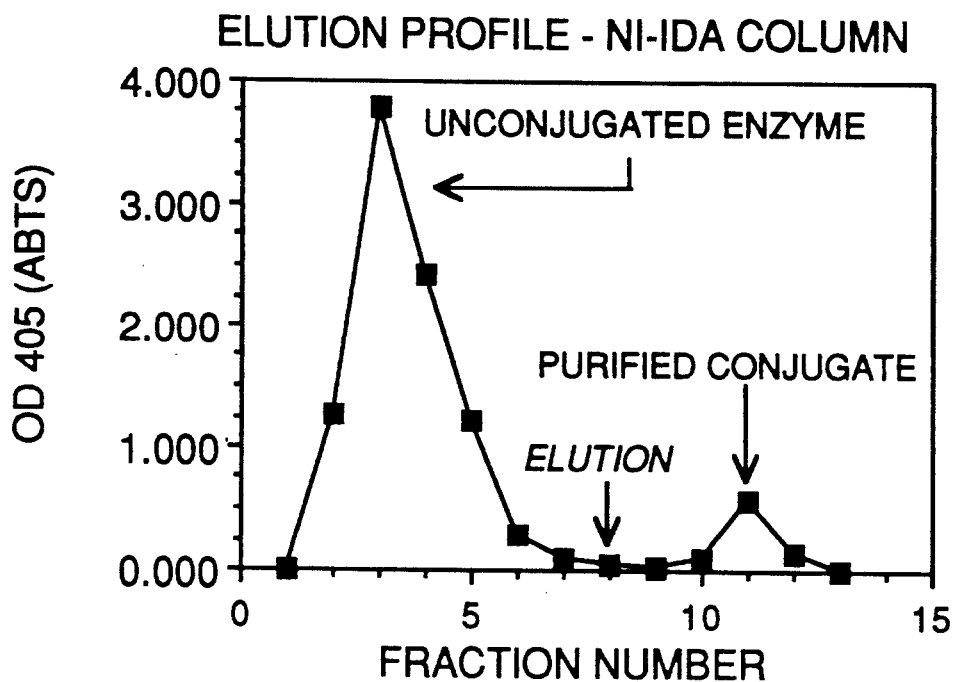
FIG. 1 is an elution profile of a separation of components accomplished in accordance with the present invention.

While metal chelate affinity chromatography on proteins is well known, a surprising aspect associated with the present invention is that with respect to the enzymes, HRP and Alk. Phos., antibody conjugates thereof will couple to the divalent metal chelating ion, $Ni^{+2}$, whereas the free enzyme will not. This phenomena is not recognized in the literature in the field of metal chelate chromatography some of which includes the following:

Porath et al., *Metal chelate affinity chromatography, a new approach to protein fractionation*, Nature Vol. 258, Dec. 18, 1975, Page 158 et seq.

Porath et al., *Immobilized Metal Ion Affinity Adsorption and Immobilized Metal Ion Affinity Chromatography of Biomaterials. Serum Protein Affinities for Gel-Immobilized Iron and Nickel Ions*, Biochemistry 1983, Page 1621-1630.

Margolis, et al., *Chromatographic Separations of Serum Proteins on Immobilized Metal Ion Stationary Phases*, Analytical Biochemistry 183, Page 108-121.

Loetscher, et al., *Immobilization of monoclonal antibodies for affinity chromatography using a chelating peptide*, 1992 Elsevier Science Publishers B.V., Page 113-119.

As indicated, the present invention utilizes a water insoluble stationary phase having the $Ni^{+2}$ ion chelated to the phase. In one aspect of this invention the stationary phase can be a water insoluble support material containing an organic chelator for divalent transition metal ions such as $Ni^{+2}$. Insoluble support materials useful in metal chelate chromatography are well known and include, support materials fashioned from, for example, agarose, polyacrylamides, silica and glass. Similarly useful organic chelators for divalent metal ions such as $Ni^{+2}$ are also recognized in the art. These include compounds with multiple carboxylic acid functionality such as iminodiacetic acid (IDA), nitrilotriacetic acid (NTA) and bicinchoninic acid (BCA).

The organic chelator can be attached to the support by conventional means which generally involves covalent attachment using a polyfunctional cross-linking reagent or direct covalent attachment using mediated coupling techniques, eg, carbodiimide or cyanogen bromide activation. Spacers, such as diaminodipropyl amine, 6 - aminocaproic acid, 1,4 -butanediol diglycidyl ether, and ethylene diamine are frequently used to separate the chelator from the support to minimize steric hindrance.

As with preparation of the insoluble support containing the metal chelating compound, chelation of the $Ni^{+2}$ ion to the support can follow known protocols. Generally the support is first equilibrated with a buffer solution followed by application of a buffer containing the $Ni^{+2}$ ion. Thereafter, the support is again washed with buffer to remove unbound $Ni^{+2}$ ion and then a buffered solution of the mixture of free enzyme and conjugate is applied to the support. After application, the support containing bound conjugate is again washed to remove unbound free enzyme.

One aspect of the present invention resides in the selection of buffers utilized in the foregoing steps, i.e., prior to elution of the conjugate from the support. These buffers should be free of compounds which can compete with $Ni^{+2}$ or the conjugate for chelating sites. Thus, metal chelators such as ethylenediamine tetraacetic acid (EDTA) or ethyleneglycol bis, beta aminoethyl ether N,N tetraacetic acid (EGTA) should not be present. Desalting of the reagents, particularly the conjugate reaction mixture, is advisable to assure the absence of competing chelators or other substances adversely affecting binding. In addition, the buffers should be mild, eg, pH 7-7.5, to avoid adversely affecting the conjugate and to achieve good conjugate bonding to the support. Tris buffered saline pH 7.2 (TBS) is a particularly useful buffer.

In order to elute the bound conjugate from the support, an elution buffer containing a metal chelating compound which displaces the conjugate on the support can be used. As indicated, EDTA and EGTA are representative examples of such compounds. However, because the enzymes in the conjugates may not be stable for prolonged period after elution with such buffers, prompt desalting after elution is preferred. While dialysis can be used, for speed the use of polyacrylamide desalting columns is preferred.

EXAMPLE I

All parts and percentages are by weight unless otherwise noted. Temperatures are at room temperature unless otherwise noted.

The following buffers were prepared:

Equilibration and Wash Buffers

TBS buffer (25 mM Tris, 150 mM NaCl, pH 7.2)

$Ni^{+2}$ Buffer (125 mM Ammonium Nickel Sulfate in 25 mM Tris, 150 mM. NaCl, pH 7.2 buffer)

To 900 ml of water, add 3.03 grams Tris followed by the addition of 8.77 grams NaCl. Stir until dissolved and adjust pH to 7.2 with Hcl and add water to obtain 1 liter. Add 50 grams nickel ammonium sulfate and stir until dissolved. The $Ni^{+2}$ buffer solution so prepared is green.

Elution Buffer (100 mM EDTA, 25 mM Tris, 150 mM NaCl, pH 7.2)

Same as preparation of $Ni^{+2}$ buffer except 37.2 grams of EDTA added instead of nickel salt, readjustment of pH to 7.2 with NaOH.

A stationary phase was prepared as follows:

20 ml of equilibration buffer was passed through a 5 ml column containing 2 ml of immobilized IDA obtained from Pierce Chemical Company, Rockford, Illinois (crosslinked 4% beaded agarose, spacer: 1,4- butanediol diglycidyl ether). Thereafter, 2 ml of $Ni^{+2}$ buffer is applied and the column allowed to equilibrate for at least five minutes to obtain binding of the $Ni^{+2}$ ion to the support. Subsequently 10 ml of wash buffer is passed through the column to remove unbound $Ni^{+2}$.

Subsequent to preparation of the stationary phase, the mixture of conjugate and free enzyme in TBS or PBS buffer is applied to the column at, for example, volumes of concentrations 0.5 ml to 50 ml., followed by 5-10 ml of wash buffer. Thereafter, 1700 μl of elution buffer is applied and a distinct blue band develops evidencing the elution front. To obtain complete elution (the blue band travels off the column) an additional 800-1100 ml of buffer is used. Thereafter, the eluted conjugate should be desalted to preserve activity.

EXAMPLE II

Following the protocol of Example I, a commercially available rabbit anti mouse IgG - HRP conjugate (raw conjugate) was purified by applying 0.5 ml of an aqueous buffered solution containing the conjugate to the stationary phase. The elution profile is illustrated in FIG. 1. Individual column fractions were tested: 150 μl of the commonly used substrate ABTS in a hydrogen peroxide containing buffer was employed. 5 μl samples of a 1:100 dilution of each fraction was employed. Substrate incubation was for five minutes, OD readings at 405 nm in an ELISA reader.

Figure 2:
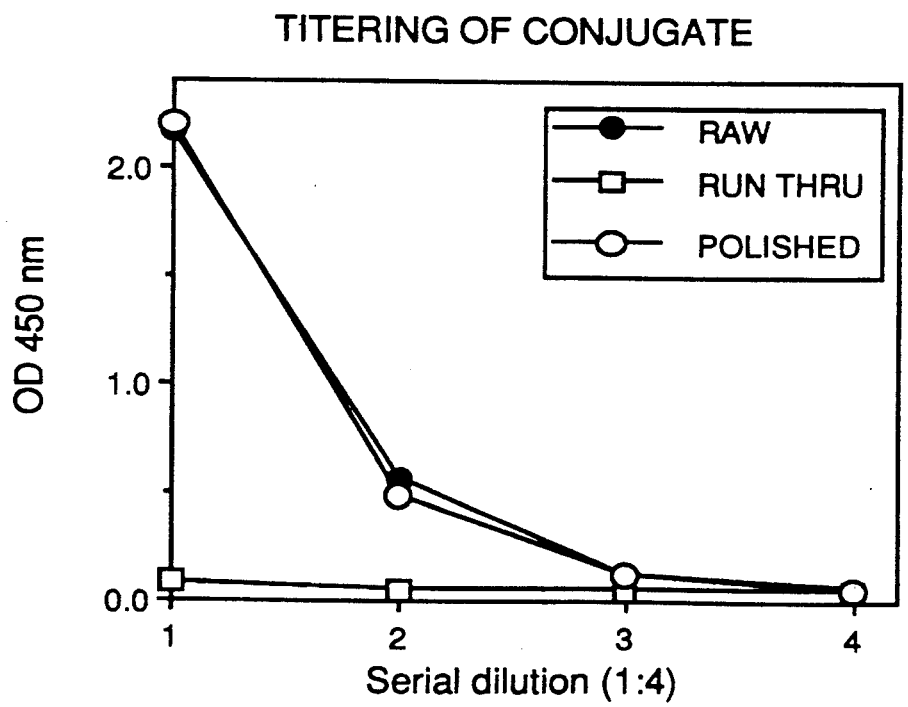
FIG. 2 is a representation of a titering of the components utilized in FIG. 1.

Referring to FIG. 1 and FIG. 2, the material that did not bind to the column (the run thru fraction) evidenced minimal IgG content as determined by ELISA testing. The content of enzyme on the other hand was very high as seen in FIG. 1. The material that did bind and was subsequently eluted (polished conjugate), evidenced almost quantitative recovery of the applied antibody as demonstrated by ELISA. The testing also indicated that the signal generating ability of the conjugate was not substantially diminished, i.e. the actual conjugate had been recovered. SDS PAGE analysis of the eluted material showed a virtual absence of free enzyme and an abundance of conjugate, thus confirming the ELISA results.

I claim:

1. A process for isolating an enzyme-antibody conjugate, wherein the enzyme is horseradish peroxidase or alkaline phosphatase, from an aqueous mixture of said conjugate and unconjugated enzyme comprising (1) contacting said mixture with a water insoluble stationary phase having the $Ni^{+2}$ ion chelated thereto and binding said conjugate to said stationary phase, (2) washing said stationary phase containing bound conjugate to remove unbound enzyme, and (3) eluting conjugate from said stationary phase and recovering the same substantially free of the unconjugated enzyme.

2. The process of claim 1 wherein the stationary phase is comprised of a water insoluble support containing an organic chelator for divalent transition metal ions with the $Ni^{+2}$ ion chelated to said organic chelator.

3. The process of claim 2 wherein the organic chelator is iminodiacetic acid, nitrilotriacetic acid, or bicinchoninic acid.

4. The process of claim 3 wherein the organic chelator is iminodiacetic acid.

5. The process of claim 4 wherein the antibody is of the IgG or IgM type.

6. The process of claim 5 wherein the water insoluble support is agarose.

7. The process of claim 6 to wherein the antibody is of the IgG type.

8. The process of claim 7 wherein the enzyme is alkaline phosphatase.

* * * * *